(12) United States Patent  (10) Patent No.: US 7,582,093 B2
Vasta et al.  (45) Date of Patent: Sep. 1, 2009

(54) SCREW EXTRACTION AND INSERTION DEVICE

(75) Inventors: Paul J. Vasta, McKinney, TX (US); Gregory A. Mohler, Pfafftown, NC (US)

(73) Assignee: AMEI Technologies, Inc., Wilmington, DE (US)

( * ) Notice: Subject to any disclaimer, the term of this patent is extended or adjusted under 35 U.S.C. 154(b) by 162 days.

(21) Appl. No.: 11/115,009

(22) Filed: Apr. 26, 2005

(65) Prior Publication Data

US 2006/0241649 A1  Oct. 26, 2006

(51) Int. Cl.
*A61B 17/58* (2006.01)
*A61B 17/60* (2006.01)

(52) U.S. Cl. ............................ 606/104; 294/99.2

(58) Field of Classification Search ............ 606/104, 606/99, 63, 69; 81/90.5, 53.2, 114, 3.43, 81/3.44, 64; 279/42, 43, 48, 50, 56, 59; 29/426.5, 29/426.4; 254/18, 20, 21, 25; 411/433, 437; 222/390; 248/73, 222.3, 231.7, 248.4, 74.1; 294/99.2, 15

See application file for complete search history.

(56) References Cited

U.S. PATENT DOCUMENTS

| 758,017 | A | * | 4/1904 | Parish ......................... 254/25 |
| 4,454,876 | A | * | 6/1984 | Mears ......................... 606/69 |
| 4,463,753 | A | | 8/1984 | Gustilo |
| 4,485,944 | A | * | 12/1984 | Eichholz ..................... 222/390 |
| 4,948,369 | A | * | 8/1990 | Braccio et al. .............. 439/347 |
| 4,977,661 | A | * | 12/1990 | Wood .......................... 29/261 |
| 5,375,956 | A | | 12/1994 | Pennig |
| 5,498,265 | A | | 3/1996 | Asnis et al. |
| 5,658,289 | A | * | 8/1997 | Boucher et al. .......... 623/13.14 |
| 5,667,513 | A | * | 9/1997 | Torrie et al. ................. 606/104 |
| 5,690,639 | A | * | 11/1997 | Lederer et al. .............. 606/104 |
| 5,951,554 | A | * | 9/1999 | Holmes ........................ 606/61 |
| 6,126,661 | A | | 10/2000 | Faccioli et al. |
| 6,183,472 | B1 | | 2/2001 | Lutz |
| 6,352,224 | B1 | * | 3/2002 | Collins ......................... 248/73 |
| 6,375,044 | B1 | * | 4/2002 | Knestout ..................... 222/151 |
| 6,473,955 | B1 | * | 11/2002 | Huang .......................... 29/268 |
| 6,524,313 | B1 | | 2/2003 | Fassier et al. |
| 7,090,680 | B2 | * | 8/2006 | Bonati et al. ................ 606/104 |

OTHER PUBLICATIONS

International Search Report of PCT/US06/15602.

* cited by examiner

*Primary Examiner*—Pedro Philogene
(74) *Attorney, Agent, or Firm*—Baker & McKenzie LLP

(57) ABSTRACT

A screw insertion/extraction device is disclosed that is useful as a tool for screw insertion and extraction procedures. The device includes a shaft sleeve that is formed to define a passage for accommodating the shaft of a wrench. In an exemplary embodiment, the shaft sleeve has a proximal portion and a distal portion interposed by an intermediate portion, where the proximal and distal portions extend along opposite sides of a central axis of the wrench shaft passage and the intermediate portion extends both along and about the central axis to connect the proximal and distal portions. A shoulder portion extends inwardly from the distal end of the shaft sleeve for engaging the base of a screw head such that the screw head can be captured between the distal end of a wrench and the shoulder portion of the shaft sleeve.

20 Claims, 5 Drawing Sheets

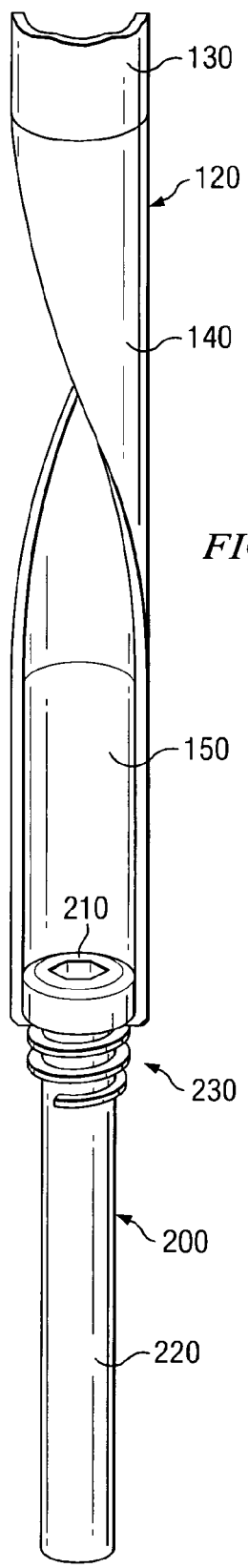
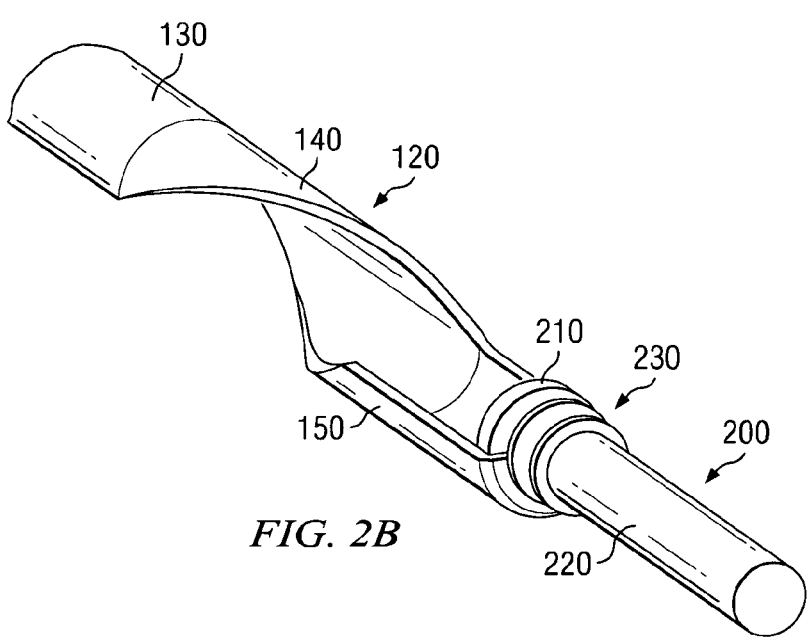
FIG. 2A
FIG. 2B

SCREW EXTRACTION AND INSERTION DEVICE

FIELD

This invention relates to tools used for the extraction and insertion of screws, having particular application in the medical field where screws are inserted and/or extracted as part of a medical procedure.

BACKGROUND

The use of bone screws for medical procedures, such as the repair of bone fractures, is known. For example, U.S. Pat. No. 4,463,753 describes a bone screw having distal threads and proximal threads. That bone screw is specifically intended for repair of a fracture by compressing the fractured segments of a bone while maintaining proper bone alignment. An end of the screw is provided with a hexagonal bore for engaging an Allen wrench, which can then be used for inserting the bone screw. However, for purposes of removing the bone screw, an Allen wrench cannot be used for exerting a pulling force for forcibly removing the bone screw.

One technique for addressing this problem is described by U.S. Pat. No. 5,375,956, which discloses a bone screw having a smooth shaft with threads near the head of the screw, as well as reverse threads extending about the head of the screw for engaging an internally-threaded extraction device. The screw can be removed by driving the extraction device onto the reverse threads to an engagement limit, at which point the extraction device can be further driven for partial extraction of the screw from the bone. Once the threads have been backed out of the bone, the screw is pulled until the remaining smooth shaft is extracted. The engagement of the internal threads of the extraction device with the external threads of the screw head allows the extraction device to be used for exerting a pulling force for extracting the smooth shaft of the screw from the bone.

However, the internally-threaded screw extractor still presents several drawbacks. For example, the use of the internally-threaded screw extractor requires the use of a screw having a threaded screw head, thus adding to the complexity and expense of manufacturing the bone screw. In addition, tissue growth often occurs in the threads of the screw head while it is in place, making it difficult to thread the extractor onto the screw for removal.

SUMMARY

In view of the shortcomings associated with the prior art, a device for screw insertion and extraction is presented herein that can be used for exerting a pulling force for removal of a screw without requiring that the screw head be threaded.

According to one aspect of the present invention, a screw extraction and insertion device comprises a shaft sleeve for engaging the shaft of a wrench. The shaft sleeve extends along a longitudinal axis, and has a proximal portion and a distal portion. The proximal and distal portions are adjacent to respective opposing sides of the wrench shaft when the shaft sleeve is engaged with the wrench shaft. The device also comprises a shoulder extending radially inward from a distal end of the shaft sleeve.

According to another aspect of the present invention, a screw extraction and insertion device comprises a shaft sleeve having a proximal portion and a distal portion connected by an intermediate portion. At least part of the proximal portion extends along a first longitudinal axis, and at least part the distal portion extends along a second longitudinal axis parallel to and offset from the first longitudinal axis. The device also comprises a shoulder that extends from the distal portion towards the first longitudinal axis.

BRIEF DESCRIPTION OF THE DRAWINGS

The present invention is illustrated by way of example and is not limited by the figures of the accompanying drawings, in which like reference numbers indicate similar parts:

FIGS. 2A and 2B show a perspective view and an enlarged perspective view, respectively, of the screw extraction/insertion device shown in FIGS. 1A-1C while engaging a screw;

DETAILED DESCRIPTION

Figure 1A:
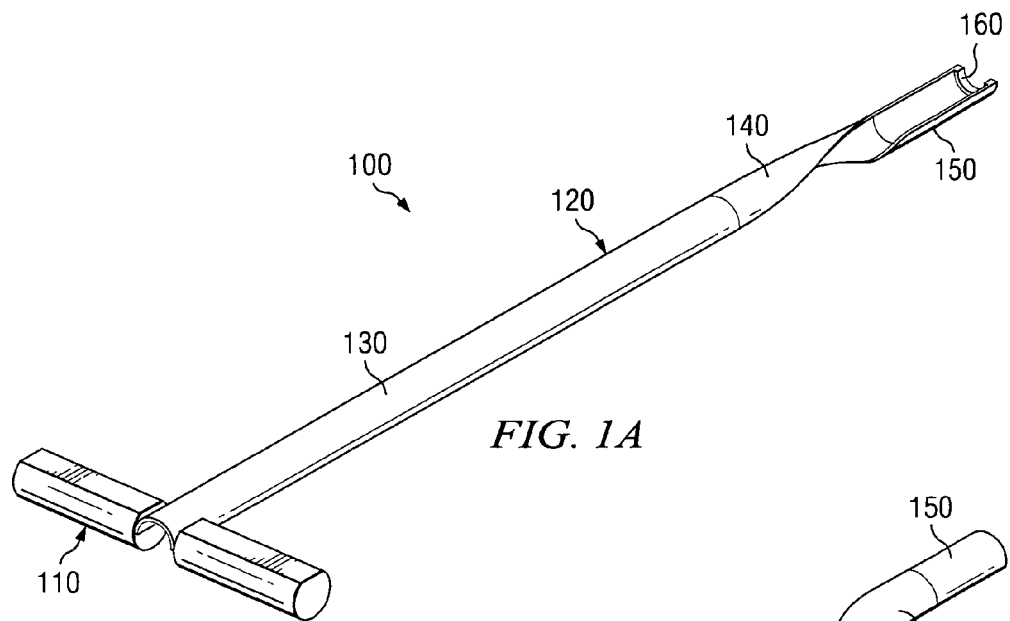
FIGS. 1A and 1B show perspective views of respective sides of a first embodiment of a screw extraction/insertion device.
Figure 1B:
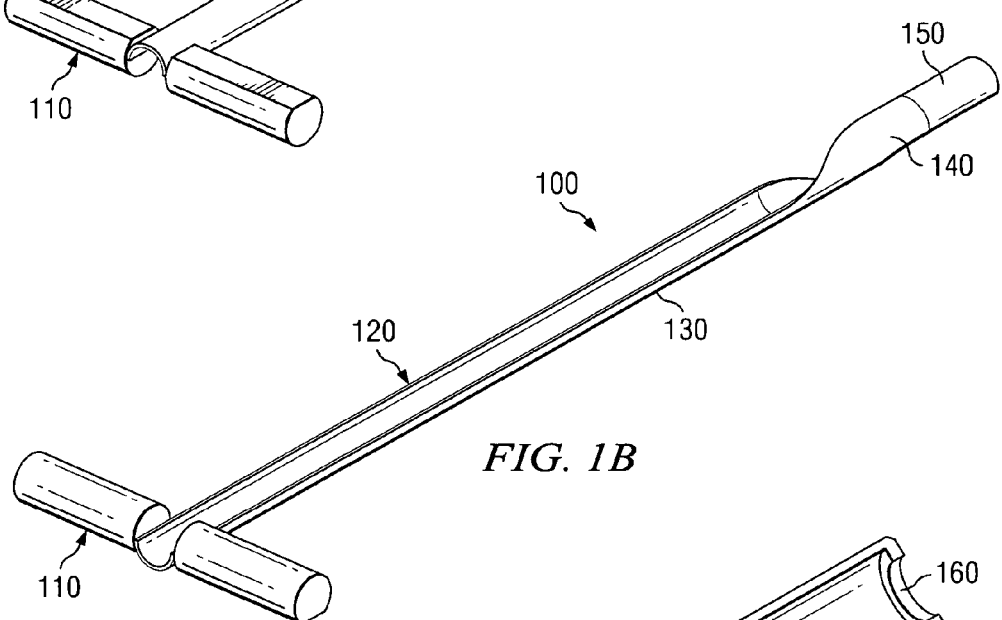
Figure 1C:
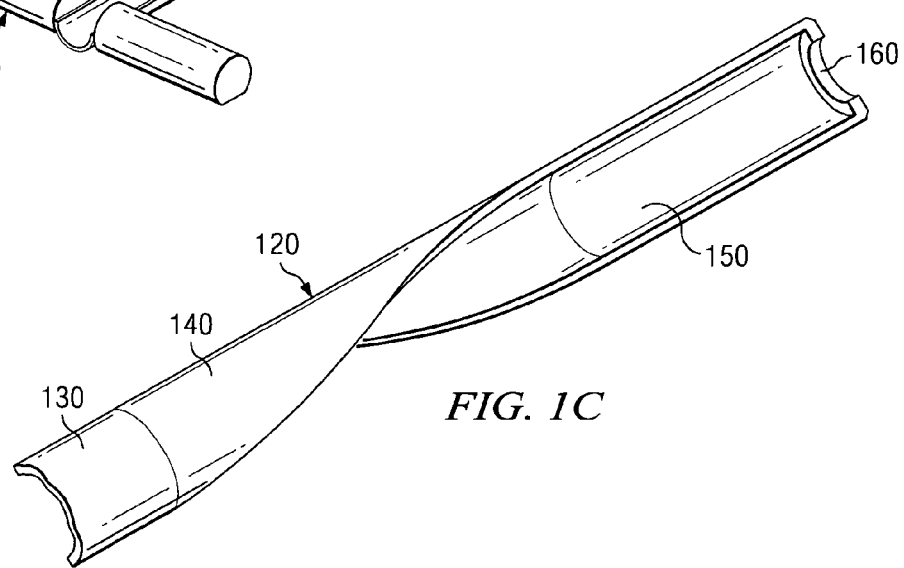
FIG. 1C shows an enlarged perspective view of a distal end of the screw extraction/insertion device shown in FIGS. 1A and 1B.

Referring to FIGS. 1A-1C, a screw extractor 100 is shown that can serve as a wrench frame for assisting in maintaining a secure coupling between a wrench and a screw. As the name implies, the screw extractor 100 is particularly useful for screw extraction procedures. However, it is important to note that the extractor 100 can be equally useful for other procedures, including screw insertion procedures. In other words, the term "extractor" is merely a term of convenience and thus is not intended to limit in any way the scope of the present invention. The screw extractor 100 is preferably constructed of a rigid material, for example stainless steel. The screw extractor 100 includes a handle 110 and a shaft sleeve 120. As shown in FIGS. 3A-3D, which are discussed in greater detail below, the shaft sleeve 120 has a form that allows it to be engaged with a wrench shaft 310 even while the wrench 300 is engaged with a screw 200.

The shaft sleeve 120 includes a proximal portion 130, an intermediate portion 140, and a distal portion 150. In the present embodiment, the proximal portion 130 and distal portion 150 are both generally semi-cylindrical in order to provide a secure interface with the cylindrical shaft of a wrench. However, it will be appreciated that alternate shapes the shaft sleeve 120 can be implemented without departing from the spirit and scope of the present invention, particularly where an alternate shape is desired for accommodating the shape of a wrench shaft. For example, the shaft sleeve 120 can include portion or portions having a parabolic, curved, curvilinear, semipolygonal (i.e., multi-faceted), U, V, or C-shaped cross section. In the illustrated embodiment the semi-cylindrical shape is preferable for providing a secure interface with a cylindrical wrench shaft (e.g., wrench shaft 310 shown in FIGS. 3A-D) and for providing a low profile for passage into soft tissue en route to a screw secured in a bone.

The semi-cylindrical component of the proximal portion 130 and the distal portion 150 are offset from each other by an angle of approximately 180 degrees about a longitudinal axis of the shaft sleeve 120. The intermediate portion 140 is generally semi-cylindrical, but forms a helical shape that twists approximately 180 degrees over the length thereof according to the angular offset between the distal portion 130 and the proximal portion 150. The proximal portion 130 can be angularly offset from the distal portion 150 by other angles about the longitudinal axis of the shaft sleeve 120, or even aligned. However, the offset as shown in FIGS. 1A-1C is preferred since it allows the shaft sleeve 120 to more securely engage the wrench shaft 310 by extending longitudinally along opposing sides of the wrench shaft 310. As best shown in FIG. 1C, a shoulder 160 is provided at a distal end of the distal portion 150. The shoulder 160 extends radially inward from the shaft sleeve 120.

The screw extractor 100 can be used for aiding in the removal and/or implantation of surgical screws. For example, the screw extractor 100 can be used for removal and/or implantation of a peg-design (i.e., smooth shaft) locking screw 200 shown in FIGS. 2A and 2B. The screw 200 can be used for fixing the position of an intramedullary nail (not shown). The locking screw 200 has a screw head 210 having a hexagonal recess 215 for driving engagement by an Allenhead wrench 300 (shown in FIGS. 3A-3D). Naturally, other types or styles of recess/wrench combinations can be used, for example slotted, Phillips, Torx, or square. The locking screw 200 also has a screw shaft 220 extending longitudinally from the screw head 210. The screw shaft 220 is smoothly cylindrical except for a threaded portion 230. The threaded portion 230 is preferably distanced longitudinally from the screw head 210 sufficiently enough to allow space for the shoulder 160 of the screw extractor 100 to engage the locking screw 200. The screw head 210 preferably has an outer diameter that is greater than an outer diameter of the screw shaft 220, or at least a portion of the screw shaft 220 adjacent to the screw head 210, in order to allow the shoulder 160 to engage the screw 200 at the base of the screw head 210. Also, the inner diameter of the distal portion 150 of the shaft sleeve 120 is preferably equal to or slightly greater than the outer diameter of the screw head 210 in order to allow the screw head 210 to be accommodated by the distal portion 150 of the shaft sleeve 120.

A method of using the screw extractor 100 for extracting a bone screw such as bone screw 200 will now be discussed in conjunction with FIGS. 3A-3D. Under typical circumstances, the locking screw 200 is removed by turning the screw counter-clockwise until the threaded portion 230 backs out of the bone 400. At this point, the screw 200 must be pulled in order to extract the smooth portion of the screw shaft 220 from the bone 400. Frictional forces between the bone 400 and the screw shaft 220 usually inhibit easy extraction. The screw extractor 100 provides a secure capture of the screw 200, particularly when used in combination with the wrench 300, for pulling the screw 200 from the bone 400. It will be appreciated that the screw extractor 100 can be similarly used for inserting the screw 200 into the bone 400.

Figure 3A:
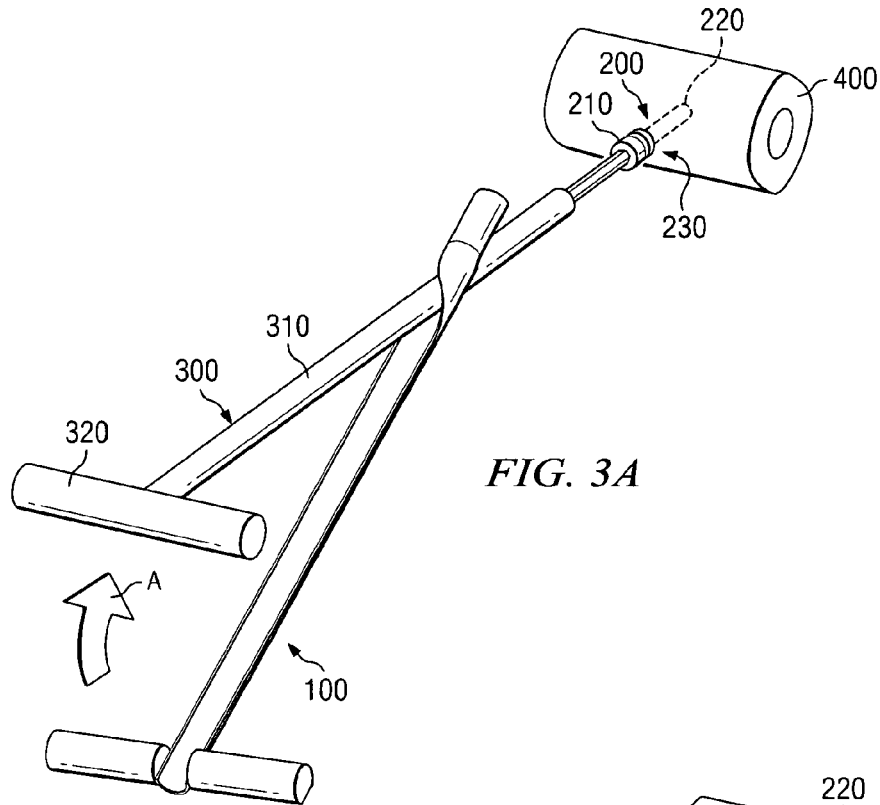
FIGS. 3A-3D show steps for engaging a screw using the screw extraction device.

In FIG. 3A, the wrench 300 is engaged with the screw 200, which has been turned to the point that the threaded portion 230 has been backed out of the bone 400. That is, in FIG. 3A the screw head 210 and threaded portion 230 are shown external to the bone 400 while the screw shaft 220 (shown in broken lines) remains in the bone. At this point, the screw extractor 100 is employed for extracting the screw 200 by pulling on the screw 200 until the screw shaft 220 exits the bone 400. As shown in FIG. 3A, the screw extractor 100 is positioned for placement over the wrench shaft 310. Specifically, the intermediate portion 140 of the shaft sleeve 120 is placed adjacent to the wrench shaft 310 with the inner side of the semi-cylindrical proximal and distal portions 130 and 150 facing the wrench shaft 310. The screw extractor 100 is initially positioned such that the shaft sleeve 120 extends at an angle to the longitudinal axis of the wrench shaft 310. Once the intermediate portion 140 of the shaft sleeve 120 is adjacent to the wrench shaft 310, the screw extractor 100 is tilted relative to the wrench 300 in the direction indicated by arrow A. The tilting motion is continued until the longitudinal axis of the shaft sleeve 120 is close to parallel with the longitudinal axis of the wrench shaft 310 as shown in FIG. 3B.

Figure 3B:
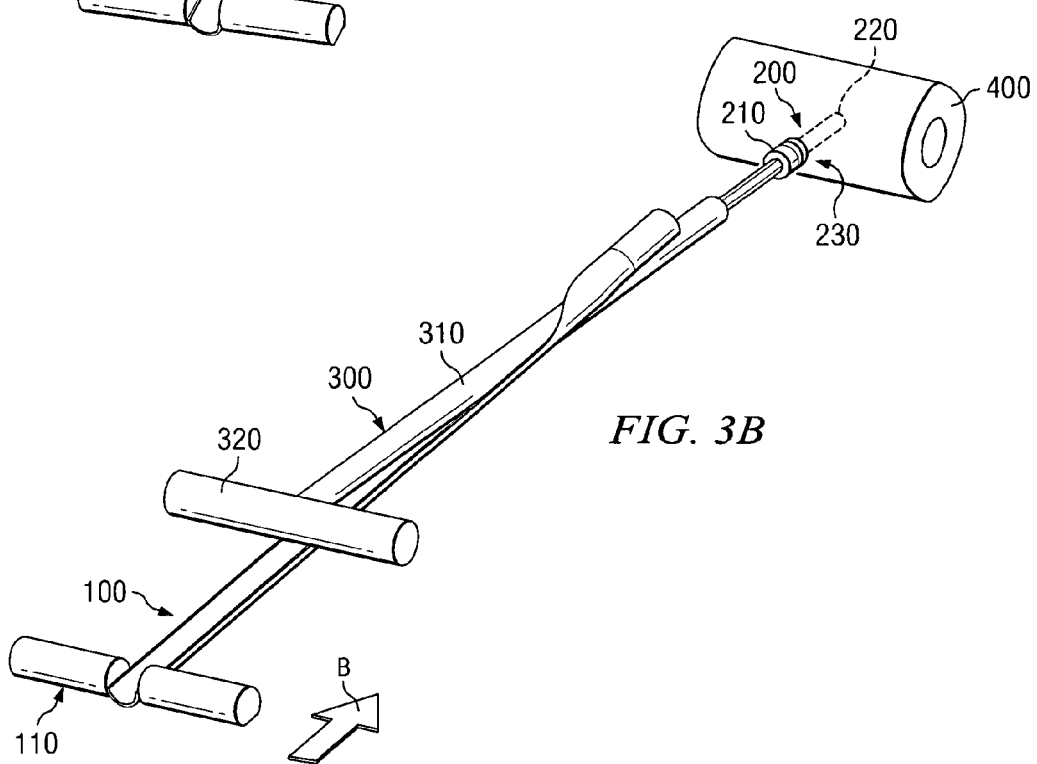

Next, as shown in FIG. 3B, the screw extractor 100 is slid along the wrench shaft 310 towards the screw 200 in the direction indicated by arrow B. The wrench shaft 310 guides the shaft sleeve 120 directly to the screw 200 so long as the shaft sleeve 120 remains in contact with the wrench 300, and the wrench 300 remains engaged with the screw 200. The screw extractor 100 is slid relative to the wrench 300 in the direction B until the handle 110 of the screw extractor 100 arrives at the handle 320 of the wrench 300.

Figure 3C:
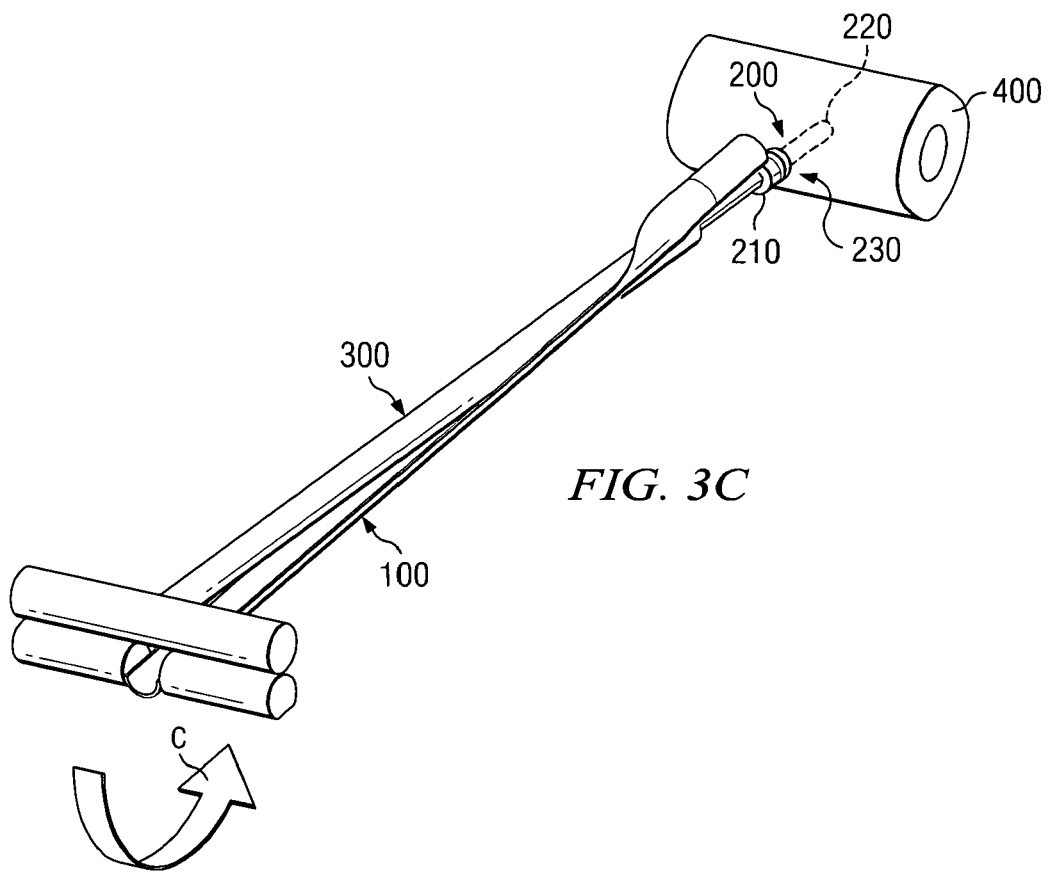
Figure 3D:
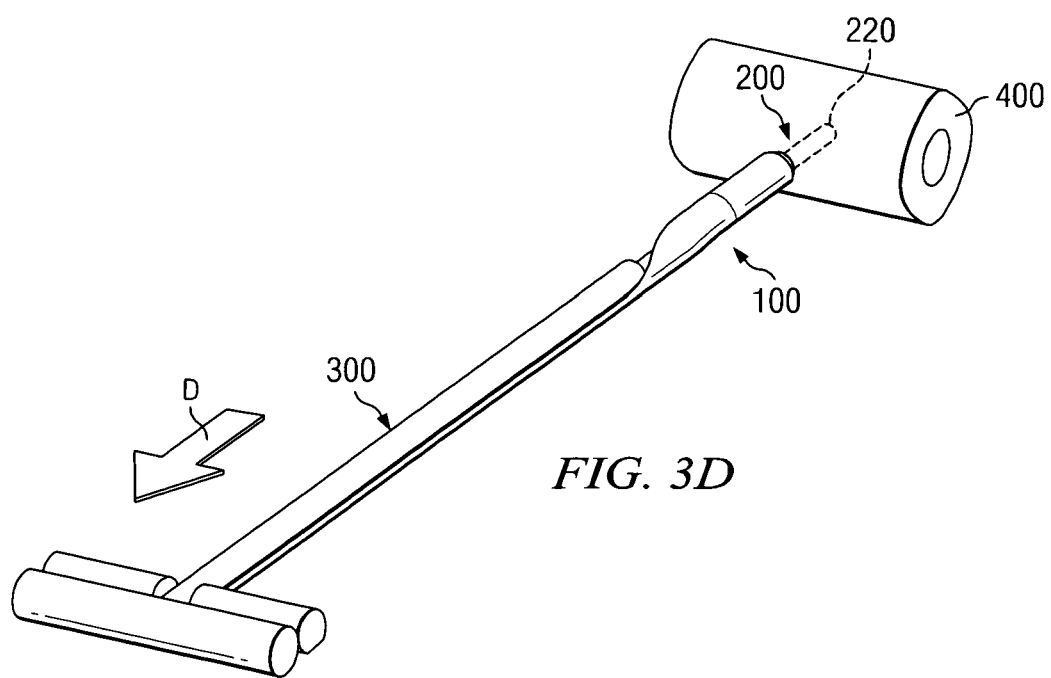

Next, as shown in FIG. 3C, the extractor handle 110 is moved under the wrench handle 320 to the position shown in FIG. 3D in a motion as generally indicated by the arrow C in FIG. 3C. The motion of the extractor handle 110 over the wrench handle 320 simultaneously moves the distal end of the shaft sleeve 120, moving the shoulder 160 of the shaft sleeve 120 behind the screw head 210. This movement captures the screw head 160, locking the screw head 210 between the wrench shaft 310 and the shoulder 160 of the shaft sleeve 120. Once the screw 200 is secured in this manner, both the screw extractor 100 and wrench 300 can be pulled as shown in FIG. 3D in the direction indicated by arrow D to extract the screw 200 from the bone 400.

As previously mentioned, the extractor 100 can also be used for screw insertion procedures. For example, the extractor 100 can be assembled with the screw 200 and the wrench 300 in order to securely capture the screw head 210 and maintain engagement between the screw 200 and the wrench 300. Once assembled, the screw shaft 220 can be pushed into a pre-drilled hole in the bone 400 to the position shown in FIG. 3D. The extractor 100 can then be removed from the wrench 300 by following the steps outlined above in connection with FIGS. 3A-3D in reverse order. The form of the extractor 100 advantageously allows the extractor 100 to be disengaged from the wrench 300 while the wrench 300 remains engaged with the screw 200. Thus, upon removal of the extractor 100 from the wrench 300, the wrench 300 can readily be used for driving the threaded portion 230 of the screw 200 into the bone 400.

Having now described an exemplary embodiment of the screw extraction/insertion device and uses therefore, it will be appreciated, particularly by those skilled in related arts, that there are numerous modifications that can be made to the screw extraction/insertion device without departing from the spirit and scope of the present invention.

Figure 4A:
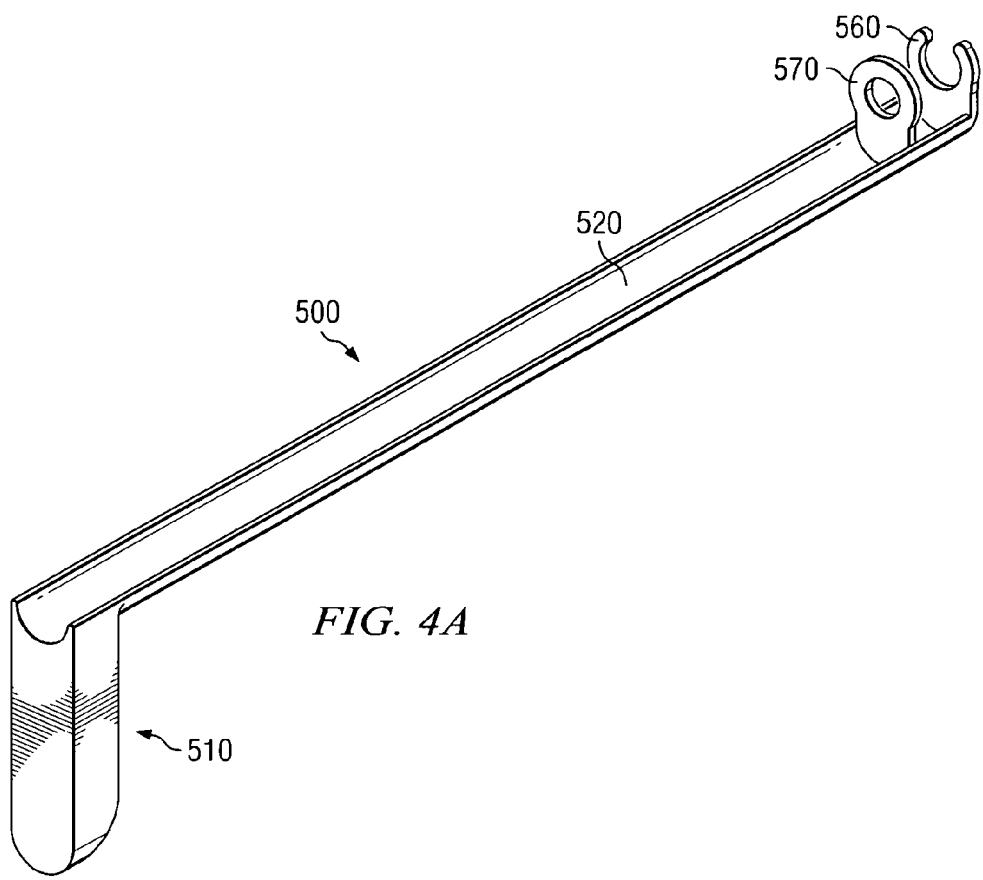
FIGS. 4A and 4B show perspective views of a second embodiment of the screw extraction device.
Figure 4B:
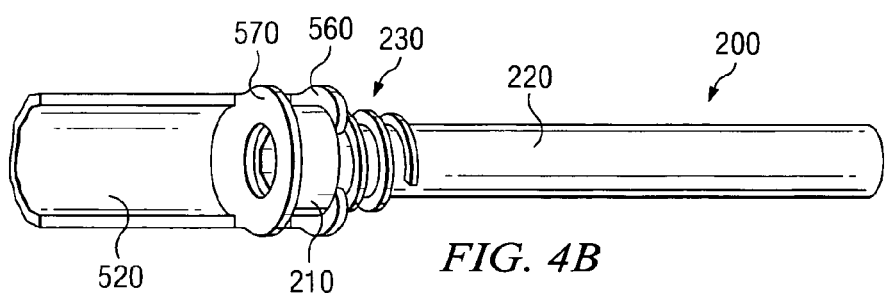

Examples of modifications that are contemplated for the screw extraction/insertion device are exemplified in an alternate embodiment—screw extractor 500—shown in FIGS. 4A and 4B. The screw extractor 500 includes modified forms of features included in the screw extractor 100, such as an alternate handle 510, shaft sleeve 520, and shoulder 560, as well as an optional collar 570. Any one or more of these modified features can be incorporated into the screw extractor 100. As shown in FIG. 4A, the shaft sleeve 520 forms a semi-circular channel that extends in a longitudinal direction between distal and proximal ends thereof. The handle 510 extends from the proximal end of the shaft sleeve 520 and the shoulder 560 extends from the distal end, the handle 510 and shoulder 560 extending in opposite directions. The shoulder 560 is a crescent-shaped member for engaging the base of the screw head as shown in FIG. 4B. The collar 570 extends from the shaft sleeve 520 longitudinally offset from the shoulder 560 by a distance sufficient to accommodate the screw head 210, allowing for the screw extractor 500 to engage the screw 200 as shown in FIG. 4B. The collar 570 assists in providing a secure coupling with the screw 200. In addition, for screw insertion procedures, the collar 570 serves as a surface for applying pressure against the screw head 210. In the embodiment shown in FIGS. 4A and 4B the collar 570 defines an aperture that allows the wrench 300 to engage and drive the screw 200. However, since the collar 570 would completely circumscribe the shaft of the wrench 300, it will be appreciated that this configuration does not allow for the screw extractor 500 to be engaged/disengaged from the wrench 300 while the wrench 300 is engaged with the screw 200. Thus, the collar 570 can instead have crescent shape similar to that of the shoulder 560, which would allow for the screw extractor 500 to be engaged/disengaged from the wrench 300 while the wrench 300 is engaged with the screw 200.

Although the present invention has been fully described by way of preferred embodiments, one skilled in the art will appreciate that other embodiments and methods are possible without departing from the spirit and scope of the present invention.

What is claimed is:

1. A screw extraction/insertion device comprising:
   a shaft sleeve having a proximal portion and a distal portion longitudinally interposed by an intermediate portion, the distal portion adapted for engaging a screw, wherein the proximal, intermediate, and distal portions are aligned with a longitudinal axis of the shaft sleeve; and
   a shoulder that extends radially inward from the distal portion towards the longitudinal axis;
   wherein the proximal portion comprises a surface that has at least two longitudinal edges,
   wherein the distal portion comprises a surface that has at least two longitudinal edges,
   wherein said surface of the proximal portion is angularly displaced about the longitudinal axis with respect to said surface of the distal portion, and
   wherein the intermediate portion comprises a surface that connects the proximal portion to the distal portion.

2. A device according to claim 1, further comprising a handle fixed to the proximal portion of the shaft sleeve.

3. A device according to claim 1, wherein the shaft sleeve is constructed of a rigid material.

4. A device according to claim 3, wherein the rigid material is stainless steel.

5. A device according to claim 1, wherein the intermediate portion includes a surface that extends along while rotating about the longitudinal axis.

6. A device according to claim 1, wherein said surface of the proximal portion and said surface of the distal portion are angularly displaced about the longitudinal axis by an angle of approximately 180 degrees.

7. A device according to claim 1, wherein at least one of the distal portion, the intermediate portion, and the proximal portion has a semi-circular cross-section.

8. A screw extraction/insertion device comprising:
   a shaft sleeve for engaging a wrench shaft that extends along a longitudinal axis, the shaft sleeve having a proximal portion and a distal portion arranged such that, when the shaft sleeve is engaged with the wrench shaft, the proximal portion and the distal portion are angularly displaced from each other along the longitudinal axis and are adjacent to opposite sides of the wrench shaft, the distal portion adapted for engaging a screw; and
   a shoulder that extends radially inward from the distal portion.

9. A device according to claim 8, further comprising a handle fixed to the shaft sleeve.

10. A device according to claim 8, wherein at least one of the distal portion and the proximal portion has a semi-circular cross-section.

11. A device according to claim 8, wherein the shaft sleeve includes an intermediate portion interposing the proximal and distal portions, wherein when the shaft sleeve is engaged with the wrench shaft the intermediate portion extends from the side of the wrench shaft adjacent to the proximal portion to the side of the wrench shaft adjacent to the distal portion.

12. A device according to claim 8, wherein the shaft sleeve is constructed of a rigid material.

13. A screw extraction/insertion device comprising:
   a shaft sleeve extending along a central longitudinal axis, the shaft sleeve including a proximal portion and a distal portion that extend along opposite sides of the central longitudinal axis and are angularly displaced from each other, the distal portion adapted for engaging a screw and the proximal portion having a handle extending therefrom, wherein the shaft sleeve further includes an intermediate portion that connects the proximal portion and the distal portion; and
   a shoulder that extends radially inward from the distal portion towards the central longitudinal axis.

14. A device according to claim 13, wherein at least one of the distal portion, the intermediate portion, and the proximal portion has a semi-circular cross-section.

15. A device according to claim 13, wherein the shaft sleeve is constructed of a rigid material.

16. A screw extraction/insertion device comprising:
   a shaft sleeve extending in a longitudinal direction from a proximal end thereof to a distal end thereof, the shaft sleeve defining a channel for accommodating a wrench shaft;
   a shoulder extending radially inward from the distal end of the shaft sleeve; and
   a handle extending from the proximal end of the shaft sleeve;
   wherein the shaft sleeve has a proximal portion and a distal portion longitudinally interposed by an intermediate portion, the distal portion adapted for engaging a screw;
   wherein the proximal portion includes a surface that extends along a first longitudinal axis; and
   wherein the distal portion includes a surface that extends along a second longitudinal axis parallel to and offset from the first longitudinal axis;
   wherein the intermediate portion includes a surface that is angularly displaced around a third longitudinal axis that is parallel to and offset from the first and second longitudinal axes.

17. A device according to claim 16, further comprising a collar extending from the shaft sleeve longitudinally offset from the shoulder.

18. A device according to claim 16, wherein the shaft sleeve is a surface having a semi-circular cross-section, said surface extending from the proximal end to the distal end along a longitudinal axis.

19. A screw extraction/insertion device comprising:
   a shaft sleeve extending along a central longitudinal axis, the shaft sleeve including a proximal portion and a distal portion that extend along opposite sides of the central longitudinal axis and are angularly displaced from each other, the distal portion adapted for engaging a screw, the shaft sleeve further including an intermediate portion that longitudinally connects the proximal portion and the distal portion, wherein the distal portion comprises a shoulder extending radially inward about the central longitudinal axis.

20. A screw extraction/insertion device comprising:

a shaft sleeve extending in a longitudinal direction from a proximal end thereof to a distal end thereof, the shaft sleeve defining a channel for accommodating a wrench shaft, the distal end adapted for engaging a screw;

a shoulder extending radially inward from the distal end of the shaft sleeve, the shoulder being substantially orthogonal to the shaft sleeve; and a handle extending from the proximal end of the shaft sleeve;

wherein the proximal and distal ends are angularly displaced from each other.

* * * * *